US008916202B2

(12) United States Patent
Lebon et al.

(10) Patent No.: US 8,916,202 B2
(45) Date of Patent: Dec. 23, 2014

(54) FLOATING MICROGRANULES

(75) Inventors: Christophe P Lebon, Rouvres (FR); Pascal J Suplie, Montaure (FR)

(73) Assignee: Debregeas et Associes Pharma, Paris (FR)

(*) Notice: Subject to any disclaimer, the term of this patent is extended or adjusted under 35 U.S.C. 154(b) by 0 days.

(21) Appl. No.: 13/390,217

(22) PCT Filed: Aug. 11, 2010

(86) PCT No.: PCT/FR2010/051691
§ 371 (c)(1), (2), (4) Date: Apr. 2, 2012

(87) PCT Pub. No.: WO2011/018582
PCT Pub. Date: Feb. 17, 2011

(65) Prior Publication Data
US 2012/0207843 A1 Aug. 16, 2012

(30) Foreign Application Priority Data
Aug. 12, 2009 (FR) ..................... 09 55641

(51) Int. Cl.
| A61K 9/14 | (2006.01) |
| A61K 31/4422 | (2006.01) |
| A61K 9/00 | (2006.01) |
| A61K 9/50 | (2006.01) |
| A61K 31/00 | (2006.01) |
| A61K 31/635 | (2006.01) |
| A61K 31/155 | (2006.01) |

(52) U.S. Cl.
CPC ........... *A61K 9/0065* (2013.01); *A61K 31/4422* (2013.01); *A61K 9/5078* (2013.01); *A61K 31/00* (2013.01); *A61K 31/635* (2013.01); *A61K 9/5026* (2013.01); *A61K 31/155* (2013.01)
USPC .............. 424/489; 424/44; 424/490; 424/494

(58) Field of Classification Search
USPC ..................... 424/44, 489, 490, 494
See application file for complete search history.

(56) References Cited

U.S. PATENT DOCUMENTS

| 4,101,650 A * | 7/1978 | Umezawa ........................ 424/44 |
| 4,424,235 A | 1/1984 | Sheth et al. |
| 5,824,339 A | 10/1998 | Shimizu et al. |
| 5,846,971 A | 12/1998 | Sangekar et al. |
| 6,214,386 B1 | 4/2001 | Santus et al. |
| 6,264,989 B1 | 7/2001 | Kato et al. |
| 6,436,438 B1 | 8/2002 | Momberger et al. |
| 7,815,934 B2 | 10/2010 | Boehm |
| 2003/0064099 A1 | 4/2003 | Oshlack et al. |
| 2005/0214372 A1 | 9/2005 | Di Capua et al. |
| 2005/0244497 A1* | 11/2005 | Sharma .......................... 424/470 |
| 2006/0039981 A1 | 2/2006 | Murpani et al. |
| 2006/0210630 A1 | 9/2006 | Liang et al. |
| 2007/0092565 A1 | 4/2007 | Aurora et al. |
| 2007/0270491 A1 | 11/2007 | Cook et al. |
| 2008/0081068 A1 | 4/2008 | Oberegger et al. |
| 2009/0011016 A1 | 1/2009 | Cailly-Dufestel et al. |
| 2009/0175939 A1 | 7/2009 | Bosse et al. |
| 2010/0249045 A1 | 9/2010 | Babul |
| 2011/0293729 A1 | 12/2011 | Lebon et al. |
| 2012/0164228 A1 | 6/2012 | Suplie et al. |

FOREIGN PATENT DOCUMENTS

| EP | 0 344 704 A1 | 12/1989 |
| EP | 0 635 265 A1 | 1/1995 |
| EP | 1 293 209 A1 | 3/2003 |
| FR | 2 829 932 A1 | 3/2003 |
| WO | WO 93/00083 | 1/1993 |
| WO | WO 00/66089 A1 | 11/2000 |
| WO | WO 01/10417 A1 | 2/2001 |
| WO | WO 01/80822 A2 | 11/2001 |
| WO | WO 02/085336 A1 | 10/2002 |
| WO | WO 03/013479 A1 | 2/2003 |
| WO | WO 2005/079760 A1 | 9/2005 |
| WO | WO 2005/101983 A2 | 11/2005 |
| WO | WO-2007/075980 A2 * | 7/2007 |

OTHER PUBLICATIONS

Mar. 30, 2011 International Search Report issued in International Patent Application No. PCT/FR2010/051691.
Rouge et al., "Buoyancy and Drug Release Patterns of Floating Minitablets Containing Piretanide and Atenolol as Model Drugs," *Pharmaceutical Development and Technology*, vol. 3, No. 1, pp. 73-84, 1998.
Elkheshen et al., "In vitro and in vivo Evaluation of Floating Controlled Release Dosage Forms of Verapamil Hydrochloride," *Pharmazeutische Industrie*, vol. 66, No. 11, pp. 1364-1372, 2004.
Sawicki et al., "Compressibility of floating pellets with verapamil hydrochloride coated with dispersion Kollicoat SR 30 D," *European Journal of Pharmaceutics and Biopharmaceutics*, vol. 60, pp. 153-158, 2005.
Sauzet et al., "An innovative floating gastro retentive dosage system: Formulation and in vitro evaluation," *International Journal of Pharmaceutics*, vol. 378, pp. 23-29, 2009.
Goole et al., "Development and evaluation of new multiple-unit levodopa sustained-release floating dosage forms," *International Journal of Pharmaceutics*, vol. 334, pp. 35-41, 2007.
Oct. 26, 2012 Office Action issued in U.S. Appl. No. 13/129,130.
Feb. 14, 2013 Office Action issued in U.S. Appl. No. 13/390,213.
Feb. 3, 2011 International Search Report issued in PCT/FR2010/051697.
Mar. 13, 2012 Written Opinion of the International Searching Authority issued in International Preliminary Report on Patentability issued in International Patent Application No. PCT/FR2010/051697.

(Continued)

*Primary Examiner* — Ali Soroush
(74) *Attorney, Agent, or Firm* — Oliff PLC

(57) ABSTRACT

The present invention relates to a floating granule comprising a solid core, on which an active ingredient is supported and also comprising a compound which is capable of generating a gas discharge which is constituted by an alkaline agent, characterized in that it does not comprise an acid agent which is capable of generating a gas discharge.

18 Claims, No Drawings

(56) References Cited

OTHER PUBLICATIONS

Jan. 15, 2010 International Search Report issued in International Application No. PCT/FR2009/052169 (with English Translation).
Written Opinion of the International Searching Authority issued in International Application No. PCT/FR2009/052169 (undated).
U.S. Office Action dated Aug. 22, 2013 from U.S. Appl. No. 13/390,213.
Lin et al., "Modification of the Initial Release of a Highly Water-Soluble Drug from Ethyl Cellulose Microspheres," J. Microencapsulation, vol. 16, No. 5, pp. 639-646, 1999.
Zou et al., "Design and Evaluation of a Dry Coated Drug Delivery System with Floating-Pulsatile Release," Journal of Pharmaceutical Sciences, vol. 97, No. 1, pp. 263-273, 2008.
Jul. 1, 2014 Office Action issue in U.S. Appl. No. 13/390,213.
Jul. 1, 2014 Office Action issued in U.S. Appl. No. 13/390,213.
PharmaTrans SANAq (Cellets—Microcrystalline Cellulose Pellets, Jul. 7, 2007).
Cellets Information Sheet, Aug. 2008, pp. 1-4.
Oct. 22, 2014 Office Action issued in U.S. Appl. No. 13/390,213.

* cited by examiner

FLOATING MICROGRANULES

The present invention relates to floating microgranules and the preparation method thereof.

Of all administration routes, the oral route remains the route of choice and therefore the one most used in the therapeutic field.

In this regard, the physiology of the gastro-intestinal tract has been widely studied in order to optimise the phenomena of absorption and elimination which regulate the pharmacokinetics of a medicament.

Thus, the gastro-intestinal tract has been modelled and studied in accordance with different parameters (transit, pH, surface-area, presence of receptors or specific transporters). In accordance with their intrinsic physicochemical characteristics, the active ingredients contained in the medication forms are absorbed at extremely precise levels of the digestive tract.

In that manner, there are different oral forms in accordance with the desired effect: slow-release form, delayed release form, bioadhesive forms allowing control of the duration and location of the release of the active ingredient.

One parameter remains difficult to control: this is gastric evacuation; it is subject to great variability which is detrimental to good reproducibility of the desired therapeutic effect. This problem is significant for medicament substances which are absorbed at a very high level in the digestive tract and results in a loss of bioavailability.

In order to overcome this, there have been put forward galenic solutions which are intended to increase the time spent in the stomach: different floating forms have thus been developed.

International application WO 01/10417 describes a pharmaceutical composition which is in the form of a tablet which floats in the stomach and which is constituted by an active phase comprising an active ingredient in association with one or more excipients and a non-active phase comprising a gas-generating system ($CO_2$) and a hydrophilic polymer or a porous mineral compound. Preferably, the generating system comprises, as an intimate admixture, an alkaline metal carbonate or alkaline-earth metal carbonate or an alkaline metal bicarbonate in association with an acid which is selected in particular from mono- and polycarboxylic acids. That intimate admixture forms an effervescent pair.

International application WO 01/80822 relates to effervescent granules and the preparation method thereof. Those granules are constituted by an effervescent pair and their hot-melt extrudable binder. The effervescent pair is a combination of an acid agent and an alkaline agent, this bringing about the formation of a gas in the presence of water. In this manner, the formulations described in WO 01/80822 comprise a combination of acid agent/basic agent.

International application WO 02/085336 relates to orally dispersible tablets which comprise at least one active ingredient, an admixture of excipients, effervescent granules which are constituted by an admixture of an acid agent, an alkaline agent and a hot-extrudable binder. Those tablets disintegrate in the oral cavity in contact with saliva in less than 60 seconds.

The works of Goole (International Journal of Pharmaceutics, 334, 2007, 35-41) describe floating mini-tablets of the encased or coated form with prolonged release. Those mini-tablets systematically contain a minimum of an active agent, a binder agent and an effervescent admixture (tartaric acid, sodium bicarbonate and calcium carbonate).

Sheth and Tossounian (U.S. Pat. No. 4,424,235) describe a floating gelatine capsule with prolonged release based on the expansion of a cellulose derivative in the presence of liquid.

In that manner, currently the great majority of the compositions set out above relate to tablets which comprise an acid/base admixture for effervescence.

However, the selection of the tablet form in the development of a floating form is not optimal because it is a monolithic form which is therefore subjected to an "all or nothing" phenomenon during gastric evacuation which further adds to the great variability.

Indeed, gastric evacuation depends on the nature, volume, size and digestibility of solids present in the stomach. Liquids but also solid particles with a diameter smaller than 3-5 mm easily pass the pylorus and will be quickly evacuated during the digestive phase. This type of particles is therefore a priori disadvantageous for the active ingredients absorbed very high in the digestive tract. For particles of larger size such as monolithic forms, they are retained by the pylorus and will be evacuated only during the inter-digestive periods.

Finally, depending on time of day (fasting or post prandial period) gastric transit for these monolithic forms will be much more consistent and can vary from a few tens of minutes to several hours.

Owing to its intrinsic form and weight, the tablet is also found to be problematic in obtaining good buoyancy of the medication form. In this case, it becomes necessary to use a large quantity of effervescent agent in order to obtain the desired buoyancy.

The above-mentioned systems must use an acid agent/basic agent pair which is capable of bringing about that effervescence which further adds to the weight and the dimensions of the tablet, and therefore ultimately inhibits the desired buoyancy. In this manner, the works of Goole mentioned above involve developing mini-tablets having a diameter of three millimeters but using an acid/basic pair for the effervescence.

The proximity of an acid agent and a basic agent within the same medication form is problematic in terms of stability and particularly under conditions of high relative humidity. That assumes the use of suitable packaging (aluminium or PVDC, or bottles with a dehydrating agent).

An object of the present invention is to provide a solution to all the above-mentioned disadvantages.

Therefore, an object is to provide an oral form which allows improvement of the bioavailability and reproducibility of the therapeutic effect for the active ingredients having a narrow absorption window or being absorbed high in the digestive tract.

Another object of the invention is the provision of a floating multi-particulate form with prolonged release which is particularly advantageous in the reduction of the variability and therefore the reproducibility and which allows avoidance of the disadvantages observed with the monolithic forms such as capsules or tablets.

Another object of the present invention is to provide a floating multi-particulate form which preserves the wall of the stomach and reduces the risks of local intolerance.

Therefore, the present invention involves the provision of a specifically developed composition to obtain a medication form which has a sufficient content of active ingredient, whilst maintaining a sufficiently small size in order to obtain satisfactory buoyancy, and most particularly for active principles with a high absorption in the digestive tract.

Therefore, the present invention relates to floating granules which comprise a solid core, on which an active ingredient is supported, the granules being characterised in that they also comprise a compound which is capable of generating a gas discharge which is constituted by an alkaline agent and does not comprise any acid agent.

Therefore, the present invention relates to floating granules which comprise a solid core, on which an active ingredient is supported, the granules being characterised in that they comprise only an alkaline agent as a compound capable of generating a gas discharge. Said compound capable of generating a gas discharge does not comprise any acid agent.

Therefore, the present invention relates to floating granules which comprise a solid core, on which an active ingredient is supported, the granules being characterised in that they comprise an alkaline agent and in that they do not comprise an acid agent, as an agent capable of generating a gas discharge.

The floating granules according to the invention are characterised in that they comprise, deposited on a solid core or support, at least one active ingredient, and in that they comprise an agent which is capable of generating a gas discharge which is constituted only by an alkaline agent.

The floating granules according to the invention therefore do not use an admixture of an acid agent/alkaline agent as usually used in the prior art. According to the present invention, the buoyancy is obtained by a reaction of the acid stomach liquid when it diffuses within the medication form.

The floating granules according to the invention are capable of floating in the stomach for a sufficiently long time and the multiple layer formulation further ensures prolonged diffusion of the active ingredient.

According to the present invention, the above-mentioned alkaline agent can also be supported on the solid support. In that manner, such floating granules according to the invention comprise, supported on the solid core, at least one active ingredient and an alkaline agent which is capable of generating a gas discharge.

According to the present invention, the above-mentioned alkaline agent can also be used directly as a support. In that manner, such floating granules according to the invention comprise, supported on a solid core, which is constituted by an alkaline agent, at least one active ingredient.

According to the present invention, the alkaline agent is used as the solid core, on which there are supported the active ingredients, or it is incorporated in the layers constituting the granule, that is to say, deposited on a solid support with the active ingredient(s) or present in a layer which is deposited above the one formed by the active ingredient(s).

Therefore, the floating granules of the invention are characterised in that they do not comprise any acid agent capable of generating a gas discharge. The term "acid agent" is intended to refer to any mineral or organic acid in the form of a free acid, acid anhydride or acid salt which is capable of generating a gas discharge. Therefore, the floating granules of the invention do not comprise any carboxylic acid capable of generating a gas discharge (that is to say, no mono- or poly-carboxylic acid).

Preferably, the floating granules of the invention do not comprise an acid agent in a quantity sufficient to allow a gas discharge.

Therefore, the floating granules of the invention are preferably characterised in that they do not comprise any acid having a pH less than or equal to 4.5 at ambient temperature.

Preferably, floating granules of the invention do not comprise tartaric acid, tartric acid, citric acid, maleic acid, fumaric acid, malic acid, adipic acid, succinic acid, lactic acid, glycolic acid, alphahydroxy acid, ascorbic acid, amino acids or salts and derivatives of those acids.

The floating granules according to the present invention have a multi-layer structure in which the active ingredient is deposited on a support and the other excipients are in turn deposited around that core.

The floating granules according to the present invention are characterized in that the alkaline agent, used as a compound capable of generating a gas discharge, is not in contact with an acidic compound.

Thus, when the floating granules according to the invention include an acidic compound, the alkaline agent and said acidic compound are separated by an intermediate layer.

The floating granules of the present invention are granules in which there is no direct contact between an acidic compound and the alkaline agent used as a compound capable of generating a gas discharge, or any other alkaline compound. Indeed, if the granules of the present invention comprise a compound of acidic character (as active ingredient or as an excipient), then they comprise intermediate films (or layers) between said acid and said alkaline agent to prevent contact between them and thus any reaction between them. The presence of such intermediate films allows to obtain stable granules. These films (or intermediate layers) play the role of protective films to improve stability.

The granules of the invention are therefore characterized by the presence of "barrier" layers increasing stability of said granules. These layers are used to prevent any reaction between the different components of said granules. They also prevent the phenomenon of effervescence before contacting the granules with the stomach medium.

According to an embodiment of the floating granules according to the present invention, the alkaline agent is deposited on the solid support: in such a case, the particles of the active ingredient and the alkaline agent are distributed similarly on the support. According to another embodiment of the floating granules according to the present invention, the alkaline agent forms another layer which is independent of the layer formed by the active ingredient.

Therefore, the alkaline agent can be incorporated at different levels of the granules. It can also be directly used as a support for the granule.

The term "granule" refers to a preparation which is constituted by dry solid grains, each forming an aggregate of powder particles having sufficient solidity to allow various operations.

From the physical point of view, the granules are aggregates of particles of different powders which are crystallised or amorphous.

The granules of the present invention are particularly intended for administration via the oral route and more particularly to be swallowed in their unprocessed state.

The granules of the present invention have a characteristic structure of the core/outer type, the core not being of the same type as the compounds forming the outer.

In that manner, those granules have a multilayer structure. The active ingredient is deposited on the core and therefore forms a layer (or outer) which is deposited around that core (or support).

The core of the granules can also be considered to be a support, to which the particles of the active ingredient will be fixed.

The core is constituted by solid particles and the active ingredient which is supported by the core is also of solid form.

Therefore, the present invention is based on developing a new multi-particulate oral form.

The granules of the invention have a layer of active ingredient.

In accordance with the final pharmacological parameters desired, that first layer may be covered by other polymer layers using different coating polymers and the different additives commonly used (plasticisers, solubilisers, lubricants, anti-adhesion agents, etc.). These layers, as described above may be protective layers, preventing the contact between the acidic and alkaline compounds.

The floating granules of the invention comprise a solid core which is preferably selected from insoluble supports, and more particularly selected from the group which consists of polyols, gums, derivatives of silica, derivatives of calcium or potassium, mineral compounds such as dicalcium phosphates and tricalcium phosphates, saccharose, cellulose derivatives, in particular monocrystalline cellulose, ethyl cellulose and hydroxy propyl methyl cellulose, starch, gluconates, silicates, sugar crystals, and admixtures thereof.

According to a specific embodiment, as indicated above, the solid core may be constituted by the alkaline agent. A specific group of granules according to the invention is therefore constituted by floating granules as defined above, in which the active ingredient(s) is/are deposited on sodium bicarbonate (constituting both the core of the granules and the alkaline agent capable of generating a gas discharge).

The solid core of the granules can also be constituted by an admixture of compounds, in particular an admixture of insoluble supports. In that manner, this particularly includes the admixture formed by saccharose and starch or mineral compounds derived from silica or calcium.

The solid core can also be constituted by soluble supports, including some solid grades of PEG (in particular PEG 4000 or PEG 6000).

The term "derivatives of silica" is intended to refer to silica and the precipitated silicas obtained from alkaline silicates, in particular Aerosil®, or talcum, bentonite or kaolin.

The term "calcium derivatives" is intended to refer to crystalline excipients which are derived from calcium hydroxide, products which are insoluble in water used in medicine as diluents, or charging agents and also abrasive agents.

The term "potassium derivatives" is intended to refer in particular to potassium bicarbonate and potassium chloride.

The insoluble supports forming the core of the granules of the invention may also include magnesium derivatives (in particular carbonates or oxides).

In the floating granules according to the invention, the alkaline agent is preferably selected from the group consisting of carbonates and bicarbonates and is particularly selected from the group consisting of sodium bicarbonate, sodium carbonate, sodium glycine carbonate, potassium bicarbonate, magnesium carbonate, calcium carbonate and admixtures thereof.

The granules of the invention may also comprise a binder.

The function of the binder is to bind the particles together, that is to say, to improve the cohesion of the granule. In that manner, the binders ensure good cohesion of the active ingredient and the core in the granules.

In that manner, the binders are deposited around the core of the granules, as is the active ingredient.

The binders may include most of the hydrophilic excipients which provide viscous solutions: gum arabic and tragacanth gum, methyl cellulose and carboxy methyl cellulose, gelatine starches, maltodextrins, PEG 4000 and 6000 in an alcoholic solution, polyvidone in an aqueous or alcoholic solution and also solutions of saccharose, glucose or sorbitol.

The binders of the granules of the invention are preferably selected from the group consisting of starch, saccharose, gum arabic, polyvinyl pyrrolidone (PVP or polyvidone), hydroxy propyl methyl cellulose (HPMC), shellac, hydroxy propyl cellulose (HPC), cellulose, polyols, polyglycolised glycerides (Gelucire®) or macrogol glycerides, particularly stearoyl macrogol glycerides, also acrylic derivatives, and admixtures thereof.

The polyols may include in particular mannitol, sorbitol, maltitol or xylitol.

According to a specific embodiment, the binders are preferably selected from the group consisting of polyvinyl pyrrolidone, shellac, polyols, polyglycolised glycerides (Gelucire®) or macrogol glycerides, particularly stearoyl macrogol glycerides and admixtures thereof.

It is also possible to use a binder selected from the groups set out above for specific properties; for example, it may be advantageous to use as a binder pH-dependent excipients such as EUDRAGIT® L100 or shellac. It is also possible to choose to use preferably polyglycolised glycerides (Gelucire®) for their hydrophobic nature.

The coated granules are constituted by grains which are coated with one or more layers of admixtures of different excipients.

In that manner, the preferred coated granules according to the present invention comprise an additional layer which is constituted by the coating agent.

According to a particular embodiment, the granules of the invention do not contain preferably any acid coating agent.

The granules of the invention may also comprise a coating which is constituted by a coating agent which is selected from the group consisting of wax derivatives, plasticisers (filmogenic agents), shellac, polyvinyl pyrrolidone, polyethylene glycol, cellulose derivatives such as HPMC or HPC, saccharose, fatty acid glycerides and methacrylic polymers.

The term "wax derivatives" is intended to refer to natural or synthetic products which are constituted by fatty acid esters and alcohols which are generally solid at ambient temperature and which are used for different purposes in medical preparations.

The floating granules of the invention may also be coated with a coating film, in which there is/are added one or more excipients such as lubricants, colouring agents, sweeteners, plasticisers or anti-adhesion agents.

The granules of the invention may also comprise an enteric coating, in particular constituted by methacrylic polymers, in particular Eudragit® L, shellac or HPMCP (hydroxy propyl methyl cellulose phthalate-hypromellose phthalate). Therefore, such granules are gastro-resistant.

The presence of that enteric coating may influence the bioavailability of the active ingredient, in particular by preventing its degradation in an acid medium.

The floating granules of the invention may also comprise a coating for prolonged release.

Such granules allow modified or delayed release of the active ingredients (modified release granules).

Such a coating is obtained with coating agents particularly constituted by co-polymers of methacrylates and acrylates Eudragit® S100, Eudragit® RS, Eudragit® RL, Eudragit® RS, Eudragit® 30D, Eudragit® RL30D, shellac, derivatives of cellulose, in particular ethyl cellulose, waxes (in particular Gelucire®) and acrylic derivatives.

The presence of this coating for modified release particularly influences the apparent half-life of the active ingredient.

The floating granules according to the present invention may also comprise a lubricant and/or a flavouring agent and/or a sweetener and/or colouring agent.

The lubricants used in the context of the present invention may include in particular talcum, magnesium stearate, silica derivatives (in particular Aerosil®) or waxes.

The flavourings used in the context of the present invention may include flavouring agents conventionally used in food additives.

The sweeteners used in the context of the present invention are particularly those set out in the directive 94/35/EC of 30 Jun. 1994 concerning the sweeteners intended for use in foodstuffs (modified by the directive 2006/25/CE of 5 Jul. 2006). In that manner, particular reference may be made to aspartame E951, sorbitol E420, mannitol E421, acesulfame-K E950, saccharine E954, stevia or thaumatin.

The colouring agents used in the context of the present invention are particularly those set out in the directive 95/45/EC of 26 Jul. 1995 concerning colouring agents which can be used in foodstuffs (modified by the directive 2006/33/EC of 20 Mar. 2006). In that manner, particular reference may be made to the colouring agents E100 to E180.

The floating granules of the invention may comprise any active ingredient used in therapeutic medicine and associations thereof. Preferably, the active ingredients used in the preparation of the floating granules of the invention are active ingredients which have a narrow absorption window or which are absorbed high in the digestive tract.

Preferably, the active ingredients are not acid compounds.

The active ingredients used in the preparation of the floating granules according to the invention may particularly include furosemide, tiapride, alfuzosin, captopril, GHB or metformin. Preferably, the active ingredient is not atenolol.

However, it is also possible to mention active ingredients having less specific absorption and, in a non-exhaustive manner, anti-viral substances, anti-depressant agents, cytostatic agents, hypocholesterolemiant agents, antalgics, anti-inflammatory analgesics, diuretics and any other therapeutic class.

The galenic form described here also has an advantage in the veterinary, nutraceutical, cosmetic and agricultural fields.

The preferred active ingredients may include antalgics and analgesics. Analgesics allow elimination of the pain of the patient. The classes of analgesics may particularly include central morphine analgesics (morphine derivatives), central non-morphine analgesics, peripheral analgesics and others such as benzodiazepines.

Preferably, the active ingredients of the granules according to the invention are selected from the group consisting of nifedipine, morphine sulphate, oxycodone, gamma-hydroxybutyric acid or one of the salts thereof, buprenorphine, modafinil, dextropropoxyphene, methadone, tramadol, nalbuphine, tetrahydrocannabinol and benzodiazepines.

According to a preferred embodiment, the floating granules according to the invention comprise from 0.5% to 60%, preferably from 15% to 50%, by weight of active ingredient in relation to the total weight of the granule.

Preferably, the floating granules of the invention comprise from 15% to 70%, preferably from 25% to 50%, by weight of alkaline agent in relation to the total weight of the granule.

Preferably, the floating granules of the invention are characterised in that the solid core represents from 20% to 80% by weight in relation to the total weight of the granule.

According to a particularly preferred embodiment, the floating granules according to the invention have a diameter which is less than 3 mm.

That size which is less than three millimeters ensures good buoyancy in the stomach liquid.

Because of this reduced size, and consequently of a reduced weight, the floating granules of the invention may easily float in the stomach liquid. They do not need to contain a great amount of compound able to generate a gas discharge ( ). It should also be stressed that granules having such a reduced size are known to present the disadvantage to have a very short residence time in the stomach. However, due to the specific structure and chemical modifications (presence of 'isolating' layers), the floating granules of the present invention do not have such a disadvantage.

In that manner, the floating granules of the invention may also be referred to as "floating microgranules".

The present invention also relates to a method for preparing floating granules as defined above, characterised in that it comprises a step of application, by powdering the active ingredient, to a solid particle support.

The method also comprises a step involving the addition of the alkaline agent.

According to a specific embodiment, the alkaline agent is added directly in admixture with the active ingredient and is powdered on the support. Therefore, such a method involves application, by powdering the active ingredient and the alkaline agent, to a solid particle support.

According to a specific embodiment, the alkaline agent is used as the solid support. In that manner, therefore, such a method involves application, by powdering the active ingredient, to the alkaline agent constituting a solid particle support.

The method of the invention may also comprise, after the powdering step, a step of coating the granule, in particular by depositing by film-coating the coating agent in the form of a film on the granule, optionally followed by a step of mixing with a lubricant and/or a flavouring agent and/or a sweetener and/or a colouring agent.

The structure of the granules of the invention is connected with carrying out that specific method which allows granules having a core/outer structure to be obtained.

The above-mentioned powdering step of the method for preparing the granules of the invention may also comprise a step of atomising an alcoholic or hydroalcoholic or aqueous solution of a binder.

That atomising step and the powdering step are preferably carried out simultaneously or alternately.

Preferably, the powdering step mentioned above is carried out in a concomitant manner with a step for atomising a binder in the form of a solution.

Combining those steps ensures good cohesion of the active ingredient on the core of the granules.

An advantageous implementation of the method of the invention thereby involves the active ingredient, which may or may not be mixed with the alkaline agent, being applied in powder form to the above-mentioned particle support (or core of the granules) in alternation with the sequences for atomising the binder in the form of a solution.

The method of the invention may also comprise, after the powdering step, one or more steps of coating the granule, in particular by the coating agent(s) being deposited by film-coating in the form of films on the granule.

A preferred embodiment of the method of the invention involves a method comprising, after the coating step, a step of mixing with a lubricant and/or a flavouring agent and/or a sweetener and/or a colouring agent, it being possible for them to be prepared in the form of granules in order finally to be mixed with the active granules.

However, the lubricants, flavourings, sweeteners and colourings can also be added before the above-mentioned powdering step.

EXAMPLES

The examples below relate to specific examples of floating granules of the invention.

Example 1

Floating Granules Based on Furosemide

|  | mg | % |
|---|---|---|
| Dry raw materials |  |  |
| Furosemide | 60.000 | 18.13 |
| Neutrals size 550-750 | 100.000 | 30.211 |
| PVP K30 | 20.000 | 6.04 |
| Gelucire 50/02 | 30.000 | 9.06 |
| Calcium carbonate | 30.000 | 9.08 |
| Sodium bicarbonate | 60.000 | 18.13 |
| Aquacoat EC30D | 25.000 | 7.55 |
| Dibutyl sebacate | 6.000 | 1.81 |
| Solvents |  |  |
| 96° alcohol | Qs |  |
| Purified water | Qs |  |
| Theoretical mass | Qs |  |
| Dry theoretical mass | 331.000 | 100.00 |
| Theoretical content (mg/g) | 181.27 |  |

The above-mentioned granules are obtained by following the operating method below.

Firstly, there is carried out an assembly step by powdering the active ingredient furosemide on the neutral supports with intermittent atomisation of an alcoholic solution of the binder PVP.

There is then carried out a first coating of the granules obtained previously by adding the alkaline agents (calcium carbonate and sodium bicarbonate) and a compound of the wax type (Gelucire®) for isolation.

Finally, there is carried out a second coating of the granules with an aqueous suspension comprising a plasticiser (dibutyl sebacate) and the coating agent Aquacoat® EC30D.

Example 2

Floating Granules Based on Nifedipine

|  | mg | % |
|---|---|---|
| Dry raw materials |  |  |
| Nifedipine | 30.000 | 11.26 |
| Sodium bicarbonate | 150.00 | 56.29 |
| HPMC 603 | 40.00 | 15.01 |
| Orange yellow S | 3.320 | 1.24 |
| Eudragit ® FS30D | 33.200 | 12.46 |
| Triethyl citrate | 3.320 | 1.24 |
| Talcum | 6.640 | 2.50 |
| Solvents |  |  |
| 96° alcohol | Qs |  |
| Purified water | Qs |  |
| Theoretical mass | Qs |  |
| Dry theoretical mass | 266.480 | 100.00 |
| Theoretical content (mg/g) | 112.57 |  |

The above-mentioned granules are obtained by following the operating method below.

Firstly, there is prepared an aqueous suspension containing the active ingredient (MOR 920) and the binder (HPMC).

The suspension has subsequently been atomised on the support which is constituted by sodium bicarbonate (alkaline agent) and the granules have subsequently been dried in a fluidised air bed.

There was subsequently carried out a coating LP of the granules previously obtained with an aqueous suspension comprising a plasticiser (triethyl citrate), talcum, the coating agent Eudragit® FS30D and the colouring agent.

Example 3

Floating Granules Based on Metformin

|  | mg | % |
|---|---|---|
| Dry raw materials |  |  |
| Metformin | 500.000 | 42.55 |
| Pearlitol 400 DC | 100.00 | 8.51 |
| GLDB | 150.000 | 12.77 |
| Ethyl cellulose/Eudragit ® E100 | 100.000 | 8.61 |
| Sodium bicarbonate | 300.000 | 25.53 |
| Precirol ® ATO 5 | 25.000 | 2.13 |
| Solvents |  |  |
| 96° alcohol | Qs |  |
| Theoretical mass | Qs |  |
| Dry theoretical mass | 1,175.000 | 100.00 |
| Theoretical content (mg/g) | 425.53 |  |

The above-mentioned granules are obtained by following the operating method below.

Firstly, there was carried out an assembly step by powdering the active ingredient furosemide on the mannitol support (Pearlitol 400DC, Roquette) with intermittent atomisation of an alcoholic solution of the binder (shellac—GLDB).

The granules were subsequently dried in a fluidised air bed.

There was subsequently carried out coating of the granules obtained previously by depositing the alkaline agent (sodium bicarbonate) and by atomising an alcoholic suspension comprising the coating agent Eudragit® E100 with ethyl cellulose and finally the compound Precirol® ATO5 (Gattefossé).

The invention claimed is:

1. A floating granule, comprising:
   a solid core on which an active ingredient is supported; and
   an alkaline agent which is capable of generating a gas discharge,
   wherein the active ingredient is selected from the group consisting of furosemide, tiapride, alfuzosin, captopril, gamma-hydroxybutyric acid, metformin, nifedipine, buprenorphine, modafinil, methadone, nalbuphine, and tetrahydrocannabinol,
   wherein, when the active ingredient is an acid compound, the floating granule further comprises an intermediate layer that separates the active ingredient from the alkaline agent, and
   wherein the solid core comprises the alkaline agent.

2. The floating granule according to claim 1, wherein the alkaline agent is not in contact with an acidic compound.

3. The floating granule according to claim 1, wherein the solid core does not comprise an acidic compound.

4. The floating granule according to claim 1, wherein the alkaline agent is selected from the group consisting of carbonates and bicarbonates.

5. The floating granule according to claim 1, wherein the solid core further comprises an insoluble support material selected from the group consisting of polyols, gums, derivatives of silica, derivatives of calcium or potassium, mineral compounds, saccharose, cellulose derivatives, starch, gluconates, silicates, sugar crystals, and admixtures thereof.

6. The floating granule according to claim 1, further comprising a binder selected from the group consisting of maltodextrins, starch, saccharose, gum arabic, polyvinyl pyrrolidone, hydroxy propyl methyl cellulose, shellac, hydroxy propyl cellulose, cellulose, polyols, and admixtures thereof.

7. The floating granule according to claim 1, further comprising a coating layer of a coating agent selected from the group consisting of shellac, polyvinyl pyrrolidone, polyethylene glycol, cellulose derivatives, saccharose, fatty acid glycerides and admixtures thereof.

8. The floating granule according to claim 1, wherein the floating granule comprises from 0.5% to 60% by weight of the active ingredient in relation to a total weight of the floating granule.

9. The floating granule according to claim 1, wherein the floating granule comprises from 15% to 70% by weight of the alkaline agent in relation to a total weight of the floating granule.

10. The floating granule according to claim 1, wherein the solid core represents from 20% to 80% by weight in relation to a total weight of the floating granule.

11. The floating granule according to claim 1, wherein a diameter of the floating granule is less than 3 mm.

12. A method for preparing a floating granule according to claim 5, the method comprising:

applying by powdering the active ingredient to the alkaline agent constituting the solid core, on which the active ingredient is supported.

13. The floating granule according to claim 1, wherein the floating granule does not contain an acid compound having a pH of less than or equal to 4.5 at ambient temperature.

14. The floating granule according to claim 1, wherein the floating granule does not contain tartaric acid, tartric acid, citric acid, maleic acid, fumaric acid, malic acid, adipic acid, succinic acid, lactic acid, glycolic acid, alphahydroxy acid, ascorbic acid, amino acid, and derivatives thereof.

15. The floating granule according to claim 4, wherein the alkaline agent is selected from the group consisting of sodium bicarbonate, sodium carbonate, sodium glycine carbonate, potassium bicarbonate, magnesium carbonate and calcium carbonate.

16. The floating granule according to claim 5, wherein the solid core further comprises a mineral compound selected from the group consisting of dicalcium phosphates and tricalcium phosphates.

17. The floating granule according to claim 5, wherein the solid core further comprises a cellulose derivative selected from the group consisting of monocrystalline cellulose, ethyl cellulose and hydroxy propyl methyl cellulose.

18. The floating granule according to claim 7, wherein the coating agent is a cellulose derivative selected from the group consisting of HPMC and HPC.

* * * * *